US009409018B2

(12) United States Patent
Tourrel et al.

(10) Patent No.: US 9,409,018 B2
(45) Date of Patent: Aug. 9, 2016

(54) DEVICE IMPLANTABLE UNDER SKIN (71) Applicant: OTICON MEDICAL A/S, Smørum (DK)

(72) Inventors: Guillaume Tourrel, Vallauris (FR); Henrik Bendsen, Smørum (DK)

(73) Assignee: OTICON MEDICAL A/S, Smørum (DK)

( * ) Notice: Subject to any disclaimer, the term of this patent is extended or adjusted under 35 U.S.C. 154(b) by 0 days.

(21) Appl. No.: 14/468,435

(22) Filed: Aug. 26, 2014

(65) Prior Publication Data
US 2015/0088226 A1 Mar. 26, 2015

(30) Foreign Application Priority Data
Sep. 26, 2013 (EP) .................................... 13186153

(51) Int. Cl.
| *A61N 1/36* | (2006.01) |
| *B23K 1/00* | (2006.01) |
| *B23K 1/20* | (2006.01) |
| *B23K 31/02* | (2006.01) |
| *B23K 1/19* | (2006.01) |
| *A61N 1/375* | (2006.01) |
| *B23K 26/32* | (2014.01) |

(52) U.S. Cl.
CPC .......... *A61N 1/36032* (2013.01); *A61N 1/3752* (2013.01); *A61N 1/3754* (2013.01); *B23K 1/0008* (2013.01); *B23K 1/19* (2013.01); *B23K 1/20* (2013.01); *B23K 26/32* (2013.01); *B23K 31/02* (2013.01); *A61N 1/3758* (2013.01); *B23K 1/0016* (2013.01); *B23K 2201/36* (2013.01); *B23K 2203/08* (2013.01); *Y10T 29/49002* (2015.01)

(58) Field of Classification Search
None
See application file for complete search history.

(56) References Cited

U.S. PATENT DOCUMENTS

| 5,782,891 | A | 7/1998 | Hassler et al. |
| 6,272,382 | B1 | 8/2001 | Faltys et al. |
| 6,456,481 | B1 * | 9/2002 | Stevenson ...................... 361/302 |
| 8,135,474 | B1 | 3/2012 | Xie |
| 8,267,708 | B1 * | 9/2012 | Sochor ................. A61N 1/3754 439/289 |
| 8,538,530 | B1 * | 9/2013 | Orinski ................ A61N 1/3754 607/36 |
| 2003/0109903 | A1 | 6/2003 | Berrang et al. |
| 2005/0159791 | A1 * | 7/2005 | Daly ................... A61N 1/36032 607/57 |
| 2006/0167534 | A1 | 7/2006 | Malinowski |
| 2009/0171420 | A1 * | 7/2009 | Brown et al. .................... 607/60 |
| 2009/0287278 | A1 | 11/2009 | Charvin |
| 2011/0029041 | A1 * | 2/2011 | Wiskerke ......................... 607/57 |
| 2011/0270067 | A1 | 11/2011 | Faraji et al. |
| 2013/0100595 | A1 * | 4/2013 | Koester et al. ........... 361/679.01 |
| 2013/0331923 | A1 * | 12/2013 | Koester .......................... 607/137 |

* cited by examiner

*Primary Examiner* — Erica Lee
(74) *Attorney, Agent, or Firm* — Birch, Stewart, Kolasch & Birch, LLP (57) ABSTRACT

A cochlear implant includes a sealed housing containing electronics for at least stimulation or collection of data and at least one antenna for communicating with an external device and a magnet configured to hold the external device in proximity to the sealed housing. The sealed housing includes an upper cover being closest to the skin when the device is implanted, and a lower cover that is hermetically connected to the upper cover. The lower cover includes an elevated region, a recessed region, and at least one feedthrough element formed in the recessed region of the lower cover. The recessed region provides space for a lead to connect to the feedthrough element and protects it from shock and other environmental risks.

22 Claims, 6 Drawing Sheets

FIG. 1

Background art

DEVICE IMPLANTABLE UNDER SKIN

TECHNICAL FIELD

The technical field relates to small connection ports, known in the art as feedthroughs, which may be used in subcutaneous active medical devices. A feedthrough element may include a conductor placed in a small opening in an electrically insulating material.

BACKGROUND

Many implantable devices use feedthrough elements to connect a hermetically enclosed electronic board to an implanted device such as a measuring and/or a stimulating electrode and/or an electromechanical actuator. A feedthrough comprises an electrical connection between a hermtically closed enclosure and the outside surrounded by insulating material, which allows electrical signals to pass between the surroundings and the hermetical enclosure while maintaining the integrity of the hermetic enclosure.

Implantable housings can be made from titanium. In the case of titanium housing, feedthroughs for the entire housing unit may be assembled into one main titanium body. The manufacturing of the titanium body thus requires a large number of welds, often at least one weld for each feedthrough.

Sometimes, each feedthrough is directly brazed onto a titanium body and requires a complex machined titanium part.

Sometimes the housing is made from alumina (aluminum oxide) which is a ceramic. Such a housing may have feedthroughs all around the outer perimeter of the ceramic. One of the technical difficulties with this design is the machining of very small holes (e.g., 0.4 mm diameter) all around the diameter of ceramic housing, which is made from a very hard material. Another issue is the cost of machining such small and precise holes, which have to be ground with diamond tools.

SUMMARY

The disclosure describes an implantable device that may be used as a cochlear implant that overcomes the challenges noted above, providing ease of manufacturing and assembly and also a unique shape of the casing that facilitates routing of connecting electrodes to the feedthrough elements through a void created between the implanted device and the tissue of a user.

In an embodiment, a device implantable under skin includes a sealed housing containing electronics for at least stimulation or collection of data and at least one antenna for communicating with an external device. The device also includes a magnet configured to hold the external device in proximity to the sealed housing. The sealed housing includes an upper cover being closest to the skin when the device is implanted and a lower cover that is hermetically connected to the upper cover, the lower cover including an elevated region, a recessed region, and at least one feedthrough element formed in the recessed region of the lower cover.

In an embodiment, the at least one feedthrough element includes a plate shaped base with one or more holes, and the at least one feedthrough element is configured to connect an electrode, providing electric connection to the electronics housed within the sealed housing through conductive pins in the one or more holes.

In an embodiment, the plate shaped base of the at least one feedthrough element is hermetically joined to the lower cover of the external housing.

In an embodiment, the lower cover has a circular disc outer perimeter shape, and the lower cover includes an elevated part located radially adjacent to the at least one feedthrough element.

In an embodiment, the elevated part is aligned radially with the at least one feedthrough element, and the elevated part is positioned farther away from a center of the lower cover.

In an embodiment, the elevated region of the lower cover has a crescent shape spanning more than 50% of the lower cover, the at least one feedthrough element is surrounded on two sides by ends of the crescent shape.

In an embodiment, the implantable device includes two feedthrough elements, each feedthrough element of the two feedthrough elements having a rectangular shape with rounded corners and having 14 connector pins.

In an embodiment, the implantable device includes two feedthrough elements, each feedthrough element of the two feedthrough elements having a circular shape and having 4 connector pins.

In an embodiment, the implantable device includes an electrically conducting lead connected to the at least one connector pin of the feedthrough element, and thereby electrically connected to the electronics in the sealed housing, a silicone overmolding surrounding the conducting lead, wherein the lead passes through a recessed region, to reach the outer circumference of the lower cover. Here the lead may connect or continue to a spirally coiled wire.

In an embodiment, the upper cover has a hollow crown made of a biocompatible material and permeable to electromagnetic waves including magnetic fields.

In an embodiment, the hollow crown includes an external wall forming an external radial periphery of the sealed housing, and an internal wall oriented towards a center of the sealed housing, and the external wall and the internal wall form an opening of an annular U-shaped groove.

In an embodiment, the biocompatible material is aluminum oxide. It is well known that other ceramics such as zirconia toughened alumina, high purity alumina, or pure zirconia could be used for this purpose but aluminum oxide has been found to be preferable.

In an embodiment, the lower cover is made of titanium. Titanium in this application denotes any titanium alloy or titanium like alloy suitable for implantation. That is any alloy which may be processed like titanium and inserted in the body without causing reaction or being degraded.

In an embodiment, the sealed housing is a cochlear implant configured to be implanted under the skin of a human user and above the user's skull bone.

The disclosure further describes a method of manufacturing an implantable device, whereby a number of manufacturing steps are performed:

form a ceramic upper cover with a circumferential flange;
    form a ceramic feedthrough element with a circumferential flange and a plurality of feedthrough pins;
    braze a feedthrough titanium welding flange leak tight onto the circumferential flange of the ceramic feedthrough element and braze an upper cover titanium welding flange leak tight onto the circumferential flange of the ceramic upper cover;
    form a titanium lower cover by stamping a titanium plate into a desired shape with a circumference an at least one opening with an edge;

weld the feedthrough titanium welding flange to the edge of the at least one opening of the titanium lower cover; and weld the titanium lower cover onto the upper cover titanium welding flange to form a hermetically sealed enclosure with a plurality of insulated electric connections.

With this method a hermetic sealed enclosure may be made with very few steps and a high yield is ensured as especially the feedthrough element may be leak tested prior to the welding thereof onto the titanium lower cover. The welding between welding flanges and titanium lower cover may be performed by laser welding to minimize heat load on nearby elements such as the feedthrough pins and the electronics within the housing. The forming of the upper cover may comprise the formation of a hollow crown including an external wall forming an external radial periphery of the upper cover, and an internal wall oriented towards a center of the upper cover, and the external wall and the internal wall thus forming an opening of an annular U-shaped groove. In this case, the brazing of an upper cover titanium welding flange onto the circumferential flange of the ceramic upper cover comprises both of the brazing of one welding flange to the internal wall and the brazing of one further welding flange to an external wall. Also the welding of the upper cover titanium weld flanges to the titanium lower cover comprises welding of both internal and external upper cover weld flanges to the lower cover.

In an embodiment of the method, forming the titanium lower cover comprises stamping elevated parts and regions and providing a recessed region relative thereto and generating the at least one opening in a recessed region. As the elevated parts and regions are intended to abut the skull of the user in the implanted state, the opening in the recessed region will be spaced apart from the skull bone of the user. This allows for feedthrough pins to extend from the feedthrough element without interfering with the skull bone.

An embodiment, the method comprise the further step of electrically connecting at least one electric lead to at least one of the metal pins outside of the hermetically sealed enclosure and cause the lead to extend in a recessed area from the pin to the outer circumference of the implantable device. At the outer circumference the leads may be joined in a spirally coiled multi-wire conductor. Thus leads may pass from the feedthrough pins to the outer regions of the housing without being subject to pressure in case the implanted housing inadvertently is pressed towards the skull bone.

An embodiment of the method comprises the further step of connecting the pins inside the implantable device to a circuit board having a plurality of interconnected electronic components thereon. This processing step may be performed prior to the closing of the hermetically sealed enclosure.

An embodiment of the method comprises the following additional steps:
place the implantable device in a mould,
hold the leads in place in the recessed area,
inject hardenable fluid material into the mould in order to form an overmould which fixates the leads.

Preferably the hardenable fluid is a silicone, which will set into a flexible but resilient protective substance, which may absorb mechanical shocks as well as insulate the leads from the corrosive nature of body fluids.

An embodiment of the method comprises the following additional step: attach in a releasable manner a magnet to an exterior part of the exterior upper cover. Preferably the magnet is provided with a casing, which interfaces with a silicone intermediate part and this intermediate part ensures a connection with the hermetically sealed housing.

DETAILED DESCRIPTION

Figure 1:
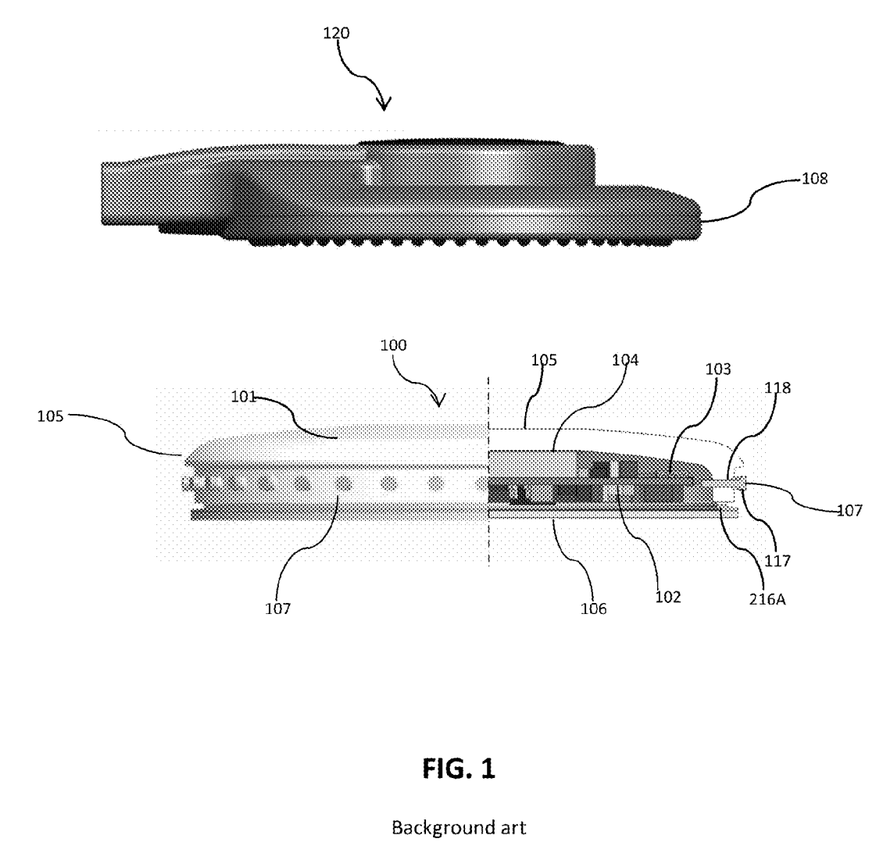
FIG. 1 illustrates a partial cross section view of an example of a cochlear implant housing with an external antenna related to the disclosure.

Neurostimulation implants can be used to stimulate and/or measure electrophysiological signals. An example of a neurostimulation implant is a cochlear implant as illustrated in FIG. 1.

The cochlear implant includes an internal portion 100 which is surgically implanted in a patient (e.g., under the skin on the skull) and an external portion 120 which attaches externally above the implanted portion. In the example of FIG. 1, the cochlear implant includes an implantable hermetic housing 101 and an external antenna 108. The implantable hermetic housing 101 includes electronics 102, a receiving/transmitting antenna 103, and a magnet 104 that holds the external portion 120 with the antenna 108 in position. The external antenna 108 can thus communicate with the electronics 102 in the implantable hermetic housing. The antennas 103, 108 may be coils, whereby magnetic energy and information may be transferred from the one coil to the other.

The design of housing 101 is based on a main body 105 made from a ceramic, such as alumina, hermetically closed with a flat titanium cover 106. The device can be implanted under a user's skin with the main body 105 oriented toward the skin (toward the outside of the user) and titanium cover oriented toward inside of the user. The titanium cover could be adjacent to the skull bone.

The main body 105 includes a plurality of feedthroughs 107 and provides mechanical protection for electronics 102, an air-tight and fluid-tight seal (hermetic seal) and electric insulation of the feedthroughs. As shown in FIG. 1, a feedthrough includes a pin made of conductive material 117 inserted into a small hole 118 formed in the main body 105.

The feedthroughs 107 are arranged radially around the outer circumference of main body 105.

Figure 2A:
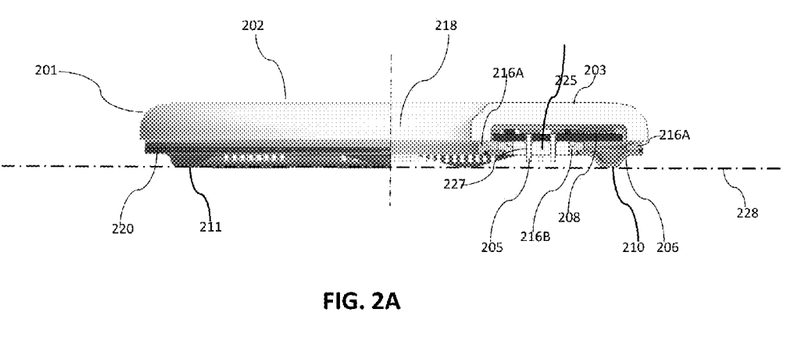
FIG. 2A illustrates a partial cross section view of an example of a cochlear implant housing according to an embodiment of the disclosure.
Figure 2B:
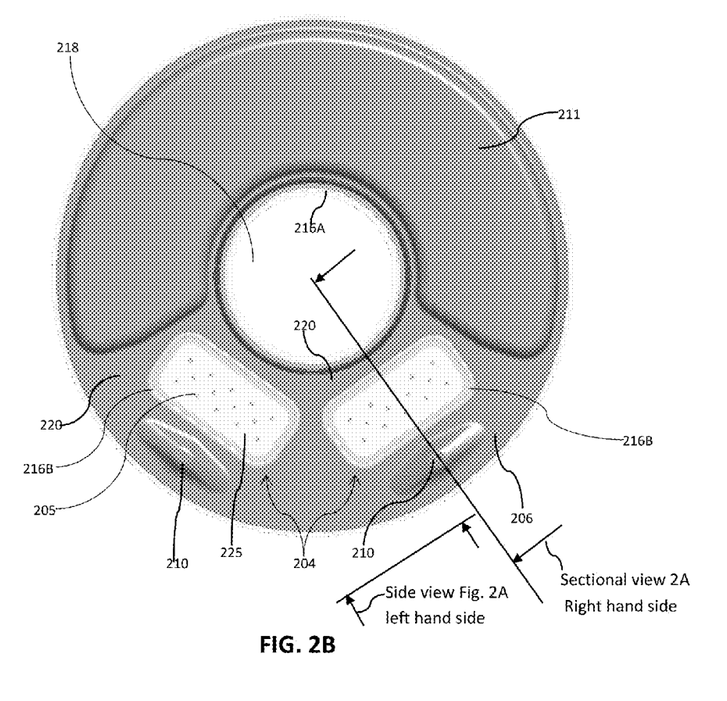
FIG. 2B illustrates a bottom view of an example of cochlear implant housing with a multipolar feedthrough element according to an embodiment of the disclosure.

FIGS. 2A and 2B illustrate another example of a cochlear implant shown without the corresponding external device. In FIG. 2A the right hand side is a sectional view, whereas the left hand side is a side-view and in FIG. 2B the section line and side view are indicated. Thus the implant is shaped as an annular object with a central hole 218 or opening. This central hole 218 serves to receive a magnet 314 as shown in FIG. 3C, which serves the same purpose as the prior art magnet 104. The implant includes a subcutaneous hermetic housing 201, which has a ceramic surface 202 on the side which faces the skin of the user, in order to allow receiving of energy by electromagnetic coupling of a coil of an external device (not shown). The implant also includes a U-shaped main body 203, made of biocompatible ceramic. The U-shaped main body 203 has a U-shaped cross sectional profile, as shown in FIG. 2A. This shape creates space within the main body to accommodate various components such as electronics board 208. The U-shaped main body 203 can be manufactured with a Ceramic Injection Molding (CIM) process and offers a solid and strong shape against multiple external constrains such as pressure, impact and shock. According to FIG. 2A, the U-shaped body is annularly shaped to circumvent the central hole 218, wherein the magnet 314 is insertable, however the magnet 314 (see FIG. 3C) could well, in an alternative thereto, be placed to circumvent the U-shaped body, in which case no central hole would be provided. Also both a centrally placed and a circumferential magnetic means could be employed.

FIG. 2B shows a view from the bottom of the cochlear implant, and displays the bottom surface of stamped titanium cover 206. The titanium cover 206 can be manufactured by stamping to obtain the desired shape.

Apart from stamping from a rolled plate item, other ways of processing the disc like item are possible, such as shaping by machining out of a solid body or by metal powder techniques. A well known powder processing techniques comprises a first step of pressing a metal powder and a binder into a semi solid body which is later heat treated or sintered into a solid metal body of the desired shape. Possibly a final machining step is necessary to achieve desired tolerances. A further powder technique uses a laser beam which melts titanium power in a layer. By repetition of layers, the part is built (like fast prototyping with polymer). A step of high temperature sintering is needed to obtain the final density on the part As shown in FIG. 2B, the stamped titanium cover 206 includes elevated parts 210 and an elevated region 211. These elevations 210, 211 are elevated relative to the plane of the cover to abut a common plane indicated by dashed line 228 seen in FIG. 3A, and thus create a recessed region 220. When the cochlear implant is implanted in a user, between skin and bony tissue (such as on the skull of the user), the elevated parts 210 and elevated region 211 abuts against the bony tissue, while there remains a void between the bone tissue and the recessed region 220. This void is useful for routing leads of electrodes from remote locations on the user's body to the implanted device. The leads can thus pass through the recessed region 220 and are protected from shock and impact by the cochlear implant supported on the elevated parts 210 and elevated region 211. As seen in FIG. 2A connection pins 205 extend out of a plate 225 and into, but not beyond the region between plane 228 and the recessed region 220.

In an embodiment, elevated parts 210 may be left out of the stamped titanium cover 206, but instead support on the skull bone may be created by the addition of a silicone distance mat, which is added on top of the recessed region of the stamped titanium cover 206. In this case the stamped cover 206 would be flat in the entire recessed region without elevated parts. The protection of the leads would be created by the silicone mat being interposed between the leads and the recessed area in that particular region. Thus, the same functionality may be provided and create a secure path for electrodes without actually shaping elevated parts 210 in the titanium cover.

FIG. 2B illustrates an embodiment with two multipolar feedthrough elements 204. In this embodiment each multipolar feedthrough element 204 includes 14 pins 205, whereby each pin forms a connection pole. The feedthrough element 204 may comprise a base shaped as a plate 225. The number of pins and the shape of the feedthrough elements are not limited to the illustrated embodiment.

Each multipolar feedthrough element 204 may be made and the holes 227 created with the use of classic processing technique for implantable devices: a ceramic plate 225 with a first and a second flat side is initially made and provided with circular holes 227 directly connecting the first and the second sides, a platinum iridium pin 205 is inserted into each hole 227, a feedthrough metal welding flange 216B preferably made from titanium is added to a circumference flange of the ceramic plate 225, and a gold brazing metal is used in a brazing process to fuse the inserted pins 205 and the titanium welding flange 216B to the ceramics of the plate 225. By this process an air and fluid tight electrically insulating plate 225 is provided with a multitude of electrical connections from the first to the second side.

By creating feedthrough elements 204 separately from the stamped titanium cover 206, it is possible to manufacture the titanium cover 206 through a stamping process and the multipolar feedthrough elements may be assembled onto the stamped titanium cover 206 by laser welding due to the feedthrough titanium welding flange 216B on the feedthrough ceramic plate 225. This example of multipolar feedthrough elements 204 has a rectangle shape with rounded edges 207 which allows a continuous laser welding process in the assembly of the ceramic plate and the titanium cover 206. In this way, feedthrough elements 204 and their connections to measuring and/or stimulation electrode leads are protected against direct constraints from the environment such as pressure, impact or shock.

Assembly of multipolar feedthrough element 204 may well be achieved by a direct mounting process such as used in surface mounted devices (SMD) where there is already a well laid out and well established process road for manufacturing in both large and smaller numbers. In the above assembly process steps, it is the process steps up to and including the fusing of the ceramic plate with the pins and metal flange which are most error prone, however, each feedthrough element comprising ceramic plate 225 with the metal pins 205 and feedthrough welding flange 216B may be tested prior to installment in the titanium cover 206, and nonfunctional parts, such as parts not being leak proof may be discarded. This is opposed to the prior art feedthrough generation, where the holes 118 are generated along the circumference of the ceramic main body 105, and in case one hole with inserted pin 117 comes out not leak proof, the entire main body has to be discarded, as an individual pin 117 is not exchangeable. This is at a time where a lot of processing hours and expensive material has been incorporated into the main body, and the result is poor yield.

FIG. 2A illustrates some internal components including electronics board 208. Electronics board 208 is mounted by the pins 205 that enter into holes of electronics board 208 before they are soldered to gain contact with the circuitry embedded in the electronic board. These pins 205 pass also through the sealed holes 227 of the feedthrough elements 204. FIG. 2E provides additional detail through an enlarged view of a cross section of the cochlear implant.

FIG. 2E illustrates an example of the construction of the implantable hermetic housing 201. Inner and outer titanium welding flanges 216A may be placed between the U-shaped main body 203 and the stamped titanium cover 206. A titanium feedthrough welding flange 216B may be placed between the feedthrough element 204 and the stamped titanium cover 206. The components may initially be brazed at brazing locations 217 in an oven to fuse the welding flanges 216A, 216B to the ceramic plate 225 and main body 203 respectively. The laser weld process finalizes the hermetically sealed hosing 201. A laser weld 211 runs along the entire circumference of the main body 203 and has a weld intersection parallel to the common plane 228. A laser weld 212 runs along the inner circumference of the main body 203 and has a weld intersection which is perpendicular to the common plane 228, and leaser welds 215 runs along the perimeter of each ceramic plate 225 of every feedthrough element and also here the weld intersection is perpendicular to the common plane 228. The advantages of the laser welds are that they are leak tight seams which may be generated without any production of fumes or gasses, and at the same time heat dissipation to brazed areas nearby or to the electronic components inside the housing 201 is manageable due to the short heating time and very limited metal melt zone. The laser welding may be performed in a controlled atmosphere to ensure that the atmosphere inside the housing 201, which will be sealed off in an airtight manner by the welding process, has well known and pre-defined properties. Preferably the gas inside the hermetic chamber is a mix of argon and helium. The argon part provides for a protective atmosphere, where as the helium gas allows for leakage test.

Figure 2C:
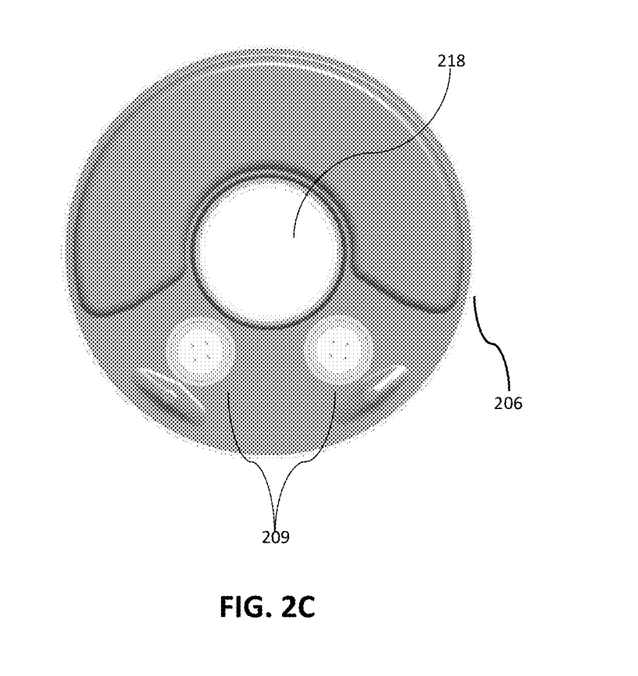
FIG. 2C illustrates a bottom view of an example of a feedthrough element with 4 connection poles in a housing according to an embodiment of the disclosure.
Figure 2D:
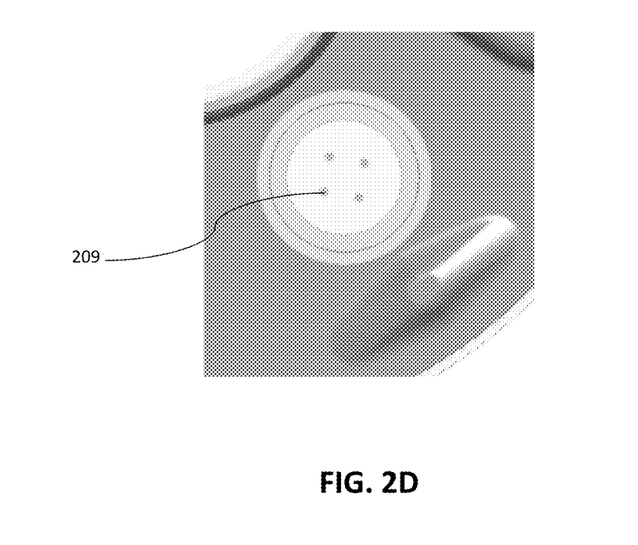
FIG. 2D illustrates a detailed view of an example of a feedthrough element with 4 connection poles according to an embodiment of the disclosure.
Figure 2E:
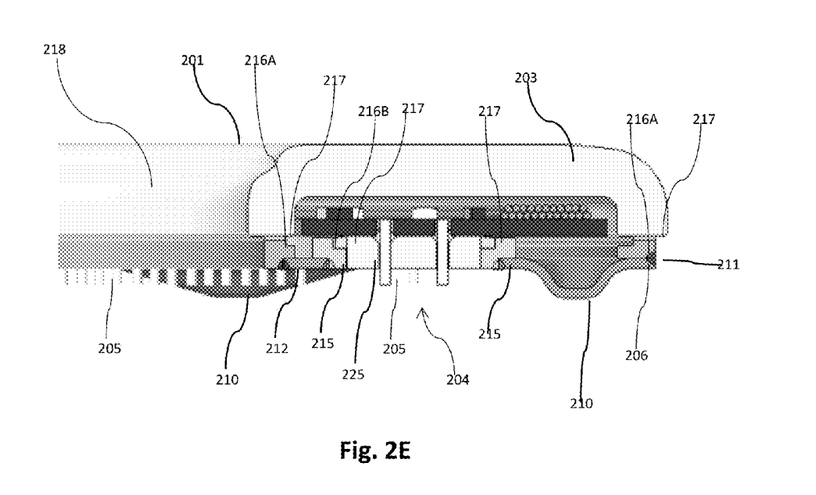
FIG. 2E illustrates an example of construction details of a cochlear implant housing according to an embodiment of the disclosure.

FIGS. 2C and 2D illustrate an example of a multipolar feedthrough element that is a quad polar feedthrough element 209 having four pins 205. The round shape of feedthrough element 209 facilitates laser welding of the feedthrough element to the stamped titanium cover 206.

An implantable connector (not shown) could be connected to the feedthrough pins 205 in order to connect leads for neuromodulation electrodes, cochlear electrode array, measuring electrodes for ECAP measures, an electromechanical actuator or antennas among others.

Figure 3A:
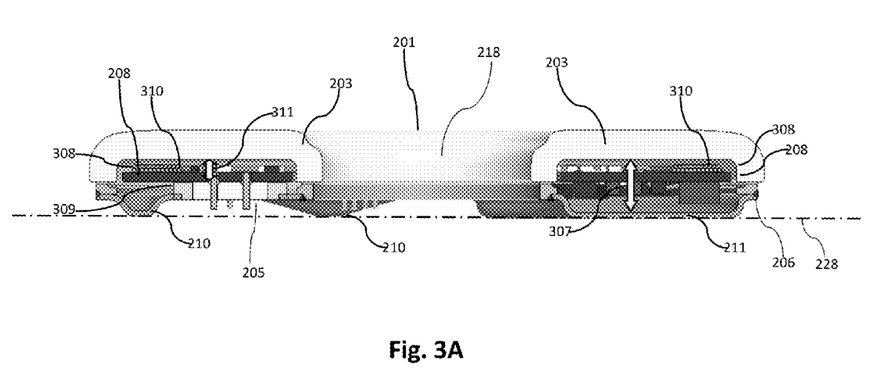
FIG. 3A illustrates a cross section view of an example of a cochlear implant according to an embodiment of the disclosure.
Figure 3B:
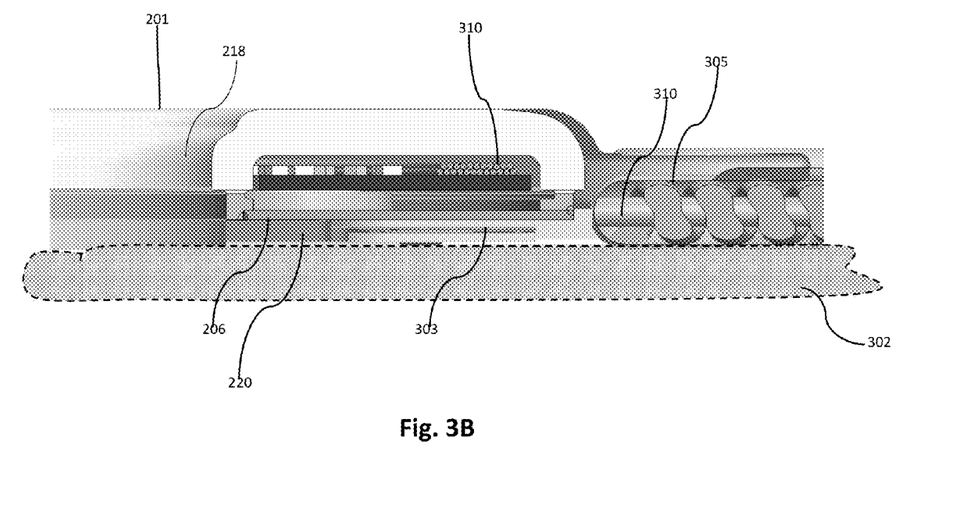
FIG. 3B illustrates an enlarged portion of the cross section view of an example of a cochlear implant according to an embodiment of the disclosure.
Figure 3C:
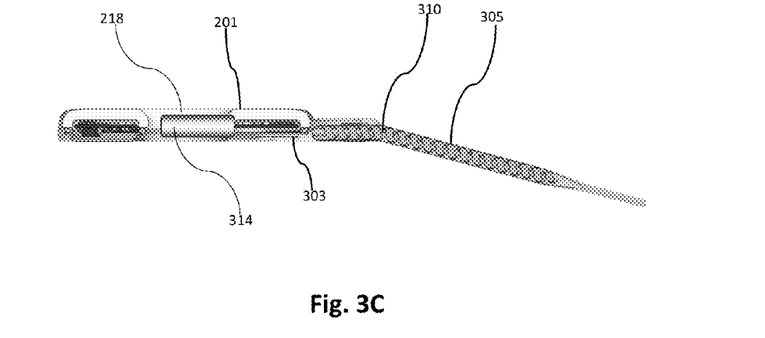
FIG. 3C illustrates a cross section view of an example of a cochlear implant according to an embodiment of the disclosure.

FIGS. 3A-C illustrates an example of additional details of components within the implantable hermetic housing 201. As shown in FIG. 3A, a voluminous area of the housing is formed between the inside of the U-shaped body 203 and the inside surface of the elevated region 211 of the stamped titanium cover 206. Arrow 307 shows the height of this area, and as seen in FIG. 3A this height allows integration of components on both sides of board 208, namely on the ceramic side 308 and on the lid side 309.

A tight area indicated by arrow 311 is defined between the ceramic plate 225 and the inside surface of the U-shaped body 203. In this area, components can be integrated only on the ceramic side 308 as the lid side 309 is reserved for the feedthrough element.

The ceramic side 308 may house an antenna 310 in order to be closest to the skin and the corresponding external antenna. The antenna 310 may be a coil. The lid side 309 can house the thickest components such as signal processors as it has the largest sectional depth 307. The coil 310 couples wirelessly with a coil provided externally of the implanted housing, and energy as well as information is transmitted, through the magnetic coupling of the two coils, from the external part to the internal part, and an information signal may pass from the coil 310 of the implanted part to the external antenna. Possibly the implanted device comprises a rechargeable battery to facilitate the transmission of a wireless signal from the implanted part to an external receiver antenna and also to supplement the energy consumed by the electrodes in times of high demand.

Alternatively or as a supplement to the antenna 310, energy harvesting by movement may be implemented as known from mechanical wrist watches: a half-circle shaped disk rotates around its centre, caused by the unbalance and the movements of the watch by the arm. This rotation winds the clock spring. Such a system may be added into the implanted device, together with the housing. Here the rotation from the half-disk is used to drive a small generator, designed to produce power and able to charge a small rechargeable battery—designed to supply the cochlear implant. The energy harvester could be designed in many ways: another example is a magnet in a tube with a coil around it, able to move back and forth according to the movement of the head. This principle is known from the battery-free so-called shake flashlights. To facilitate the smaller size of the implant, the rotating system may be placed in a separate cabinet, implanted elsewhere in the head and connected to the cochlear implant through a wire. If the implant is placed right under the skin, a solar cell in the unit could add energy for charging during the day. However, the skilled person would appreciate that the energy harvester may also be placed at a different location in-vivo.

As shown in FIG. 3B, the recessed region 220 forms a space between the stamped titanium cover 206 and the skull bone tissue 302. The wires or leads 303 which connect the pins in the feed-through to a device external to the housing 201, such as to electrodes, sensors, antennas or transducers pass in this space wherein they are protected against shock and impact by a silicone overmolding 304 as seen in FIG. 3C and by the elevated parts and regions.

As seen better in FIG. 3C, the leads 303 pass out from the region of the housing and form a spiral 305 which is able to absorb forces that could be applied to the lead 303. The spiral 305 is able to be stretched, folded and bend and can thus adapt to the individual surgery and the shape of the mastoidectomy as well as adapt to cranial growth and other changes which may take place after surgical implant of the device. The spiraled coil is wound around a pin, which is then drawn out to leave a void 310 at the center of the spiraled coil. Along the spiral, placed inside the void 310 left by the pin, or outside it such as along the ground electrode an antenna lead for FM communication may be placed. Also possibly any of the ground electrode, a measuring electrode, a stimulation electrode, or a lead passing over the top of the head to an implant at an opposed side of the head, may be used additionally as a radio antenna. Any inside or outside surface of the implanted housing or the circuitry board 208 may serve as a carrier for a radio frequency antenna such as a patch antenna or a rod antenna. Such antennas could allow the implanted part to communicate with external units by Bluetooth or similarly coded protocols, which could provide a wider band-width of the communication between external part and implanted part, than what is obtainable by means of the coil 310. This requires an additional radio to be incorporated into the internal part. The higher frequencies used in usual RF transmission of information lead to a high degree of attenuation when transmitted through human tissue, however, the external antenna part and the implanted part are placed in very close proximity and are also located in well known positions with respect to each other, which allows for antenna designs with a high degree of directionality to be used, and also their closeness to each other situates the external and internal antennas within the near field of each other, and these two fact may ensure very good coupling between such two antennas, and this may overcome the problems of attenuation of the RF frequency signals transmitted through the tissues of the user. A similar argument goes for RF frequency transmission of signals between two implanted devices placed at each side of the head, whether the signals are transmitted directly from implanted part to implanted part, or signals are exchanged from one external part to the other, or from one external part to both of two implanted parts being placed at each side of the head of a user. One particular frequency band which would be open to such communication RF signals would be the band around 2.4 GHz used for Bluetooth and Bluetooth low energy transmission. A patch antenna with a directional characteristic is disclosed in WO2007019855 and such an antenna could be used.

The potential mix-up of the two BTE and antenna parts for the respective left and right ear can cause problems for users with an implant at each ear, because of differences in the two implants and/or stimulation schemes for the left and right ears. Also in school classes with many pupils carrying similar implant and external parts, such a mix-up may take place between pupils. An ID-chip, such as an RFID chip in each implanted part for identification is available and need only to communicate a short distance to the BTE (Behind The Ear) part or to the antenna part and to such a purpose only limited power and a small antenna is needed. A simple hand-shake procedure between external part and implant may be instigated prior to on-set of transmission of sound signals, to ensure that it is the correct external part, and not a part belonging to the other ear or a school friend. The identification hand shake may take place by means of the coil antennas in the external and internal parts, however here the communication is not so fast. In US2005/0255843A such an identification scheme is disclosed, which allows proprietary communication using magnetically coupled coils between two separate devices, such as a first and a second hearing aid sitting on each one of a users ears. This technique could also be implemented and used between an implanted part and an external part, provided the internal part has some energy storage capacity, eg a battery, which would allow it to transmit its own identification code to the external part when prompted.

Figure 3D:
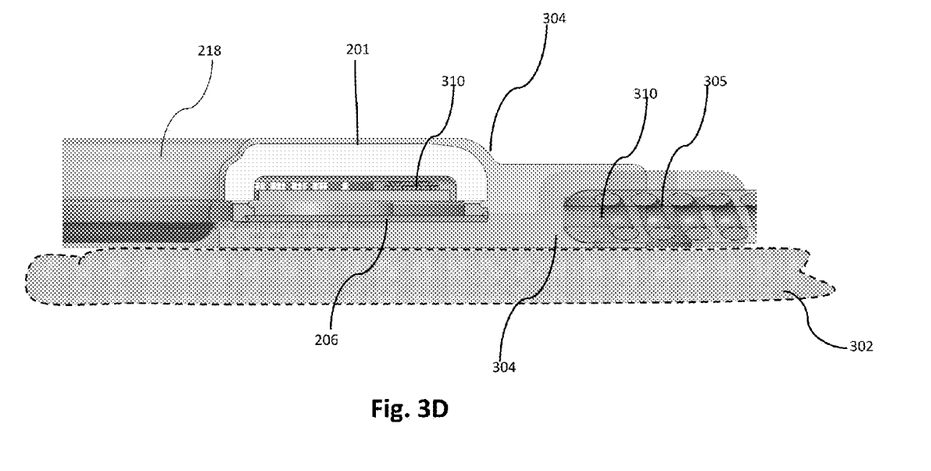
FIG. 3D illustrates a cross sectional view corresponding to FIG. 3B, but now with the a mold over silicone shealding.

FIG. 3D shows how the overmold with a hardenable substance such as silicone encapsulates the housing 201. The silicone fills the void made under the housing by the recesses and elevated parts of the titanium cover 206 whereby all leads in the area are fixated and protected both against shock and tissue fluids of the body. Also al the pins of each feed-through are completely embedded in the silicone and thereby protected.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

List of Elements:
100 internal portion
101 implantable hermetic housing
102 electronics
103 receiving antenna
104 magnet
105 main body from ceramic
106 flat titanium cover
107 feedthrough
108 external antenna
117 conductive material pin
118 small hole
120 external portion
201 subcutaneous hermetic housing
202 ceramic surface
203 u-shaped main body
204 multipolar feedthroughs
205 pin(s)
206 stamped titanium cover
207 rounded edge
208 electronics board
209 quad polar feedthrough
210 elevated part
211 elevated region
212 outer laser weld
213 inner laser weld
215 feed through laser welds
216A upper cover titanium welding flange
216B feedthrough titanium welding flange
217 brazing locations
218 central hole
220 recessed region
225 ceramic plate
227 hole
228 common plane
302 skull
303 wires
304 silicone overmolding
305 spiral
306 lead
307 voluminous area arrow
308 ceramic side
309 lid side
310 antenna
311 tight area arrow
314 exchangeable magnet

The invention claimed is:

1. A device implantable under skin, comprising:
a sealed housing containing electronics for at least stimulation or collection of data and at least one antenna for communicating with an external device,
wherein
the sealed housing includes
an upper cover being closest to the skin when the device is implanted, and
a lower cover that is hermetically connected to the upper cover along a boundary, the boundary defining a plane,
the lower cover includes
at least one elevated region having an outer surface substantially parallel to the plane and positioned farther away from the upper cover than an outer surface of a recessed region of the lower cover,
the recessed region having its outer surface substantially parallel to the plane,
at least one feedthrough element formed in the recessed region of the lower cover, and
an elevated part located adjacent to the at least one feedthrough element, the elevated part having substantially same height relative to the plane as the elevated region.

2. The device according to claim 1, wherein
the at least one feedthrough element includes a plate shaped base with one or more holes, and the at least one feedthrough element is configured to connect an electrode to the electronics housed within the sealed housing through conductive pins in the one or more holes.

3. The device according to claim 2, wherein the plate shaped base of the at least one feedthrough element is hermetically joined to the lower cover of the external housing.

4. The device according to claim 1, wherein the lower cover has a circular disc outer perimeter shape defining said boundary.

5. The device according to claim 4, wherein the elevated part is aligned radially with the at least one feedthrough element, and
the elevated part is positioned farther away from a center of the lower cover.

6. The device according to claim 4, wherein the elevated part has an outer surface that is substantially parallel to the plane of the boundary, and
said at least one feedthrough element has a length that does not extend beyond the outer surface of the elevated part.

7. The device according to claim 4, wherein the elevated part includes a sloped wall terminating in a flat top, the flat top being coplanar with the outer surface of the elevated region.

8. The device according to claim 4, wherein the elevated region of the lower cover has a crescent shape bound by two partial arcs of concentric circles with different radii centered at the center of the lower cover.

9. The device according to claim 8, wherein each of the two partial arcs spans more than 50% of the circumference of its respective concentric circle.

10. The device according to claim 4, wherein the elevated part is distinct from the elevated region.

11. The device according to 1, further comprising:
an electrically conducting lead connected to at least one connector pin of the feedthrough element, and thereby electrically connected to electronics in the sealed housing;
a silicone overmoulding surrounding the conducting lead, wherein the lead passes through the recessed region of the lower cover, to reach an outer circumference of the lower cover.

12. The device according to claim 1, wherein the upper cover has a hollow crown made of a biocompatible material and permeable to electromagnetic waves including magnetic fields.

13. The device according to claim 12, wherein the hollow crown includes
an external wall forming an external radial periphery of the sealed housing, and
an internal wall oriented towards a center of said sealed housing, and
the external wall and the internal wall form an opening of an annular U-shaped groove.

14. The device according to claim 13, wherein the biocompatible material is aluminum oxide.

15. The device according to claim 14, wherein the lower cover is made of titanium.

16. The device according to claim 1, wherein the sealed housing is a cochlear implant configured to be implanted under the skin of a human user and above the user's skull bone.

17. The device according to claim 1, wherein said at least one feedthrough element includes at least one pin extending substantially perpendicularly to the plane of the boundary.

18. The device according to claim 17, wherein said at least one pin has a length that does not extend beyond a height of the elevated region relative to the plane of the boundary.

19. The device according to claim 1, wherein the at least one feedthrough element is located in said outer surface of the recessed region.

20. A device implantable under skin, comprising:
a sealed housing containing electronics for at least stimulation or collection of data and at least one antenna for communicating with an external device, wherein
the sealed housing includes
an upper cover being closest to the skin when the device is implanted, and
a lower cover that is hermetically connected to the upper cover along a boundary, the boundary defining a plane,
the lower cover includes
at least one elevated region having an outer surface substantially parallel to the plane and positioned farther away from the upper cover than an outer surface of a recessed region of the lower cover,
the recessed region having its outer surface substantially parallel to the plane, and at least one feedthrough element formed in the recessed region of the lower cover,
the elevated region of the lower cover has a crescent shape bound by two ends and by two partial arcs of concentric circles with different radii centered at the center of the lower cover, the partial arcs spanning more than 50% of the circumference of the concentric circles, and
the at least one feedthrough element is surrounded on two sides by said two ends of the crescent shape.

21. The device according to claim 20, comprising:
two feedthroughs, each feedthrough of said two feedthroughs having a rectangular shape with rounded corners and having 14 connector pins.

22. The device according to claim 20, comprising:
two feedthrough elements, each feedthrough element of said two feedthrough elements having a circular shape and having 4 connector pins.

* * * * *